United States Patent [19]

Schrier

[11] Patent Number: 5,037,650

[45] **Date of Patent: * Aug. 6, 1991**

[54] LIVE COMBINATION VACCINE

[75] Inventor: Carla C. Schrier, Boxmeer, Netherlands

[73] Assignee: Akzo N.V., Arnhem, Netherlands

[ * ] Notice: The portion of the term of this patent subsequent to Jun. 14, 2005 has been disclaimed.

[21] Appl. No.: 165,339

[22] Filed: Mar. 8, 1988

Related U.S. Application Data

[63] Continuation-in-part of Ser. No. 462,221, Jan. 31, 1983, Pat. No. 4,751,079.

[51] Int. Cl.$^5$ .......................... A61K 39/12; C12N 7/00

[52] U.S. Cl. .......................................... 424/89; 424/86; 424/88; 435/235.1; 435/236

[58] Field of Search .............................. 424/89, 86, 88; 435/235, 236, 235.1

[56] References Cited

U.S. PATENT DOCUMENTS

| | | | |
|---|---|---|---|
| 2,798,835 | 7/1957 | Markham et al. | 424/89 |
| 4,751,079 | 6/1988 | Burger et al. | 424/84 |

*Primary Examiner*—Margaret Moskowitz
*Assistant Examiner*—Abdel A. Mohamed
*Attorney, Agent, or Firm*—William M. Blackstone; Donna Bobrowicz

[57] ABSTRACT

The present invention is concerned with live combined vaccines for immunizing poultry comprising at least two different viruses, wherein at least one of the viruses is an infectious bronchitis virus showing the property of spontaneously hemagglutinating chicken erythrocytes.

10 Claims, No Drawings

LIVE COMBINATION VACCINE

This application is a continuation-in-part of application Ser. No. 462,221, filed Jan. 31, 1983, with a priority date of Feb. 5, 1982, and which is now U.S. Pat. No. 4,751,079 and which is herein incorporated by reference.

TECHNICAL FIELD

The invention is concerned with live combination vaccines containing infectious bronchitis viruses.

BACKGROUND

Infectious Bronchitis Virus (IBV) is a Corona virus which is infectious to birds and in particular to poultry. Infection with the virus results in an acute respiratory disease, characterized by trachea rales, coughing, sneezing and nasal discharge. Infectious bronchitis (i.b.) may cause a considerable mortality among afflicted chickens, and moreover may damage their kidneys. In layer and in breeder hens the infection may cause a drop in egg production due to damage of the reproductive tract. In many cases the egg drop is accompanied by an enteritis causing diarrhea.

Poultry can be protected against IBV infections by vaccination. Moreover, there is a desire to protect the birds at as early an age as possible. These young chickens are also vulnerable to infection by other viruses, such as Newcastle Disease Virus (NDV), Infectious Bursal Disease Virus (IBDV), Marek's Disease Virus (MDV), other avian Herpes Viruses, Fowl Pox Virus (FPV), Avian Encephalomyelitis Virus (AEV), Reticulo-endoteleosis Virus (REV), avian Adeno Viruses and avian Reo Viruses. Of course, there is a desire to protect the young chickens not only against IBV infection but to protect them against infections by other of the abovementioned viruses as well. To this end, young chickens have been vaccinated with vaccines comprising combinations of immunogens derived from IBV as well as from at least one of the other viruses. These vaccines may contain live or inactivated viruses, but in principle live vaccines are favored. A well known problem with these live combination vaccines is the mutual influence of the antigenic components resulting in a decrease of the potency of one or more of the constituting components. This problem has been reported for the combination IBV/NDV by e.g. Raggi & Lee (1964) Avian Disease 8, 471–480; Hanson & Alberts (Am.J.Vet.Res. March 1959, 352–356) and Thornton & Muskett (The Veterinary Record, May 1975, 467–468); conflicting results were published by Winterfield (Poultry Science 1984, 63, 182–184).

SUMMARY OF THE INVENTION

It has been found now that the shortcomings of the known live combined virus vaccines described above can be overcome by employing the novel vaccine according to the present invention. This live combined vaccine is characterized in that it comprises at least one live infectious bronchitis virus showing the property of spontaneously hemagglutinating chicken erythrocytes together with at least one other virus infectious to poultry. IBV's having the property to spontaneously hemagglutinate chicken erythrocytes are known to possess superior vaccinating properties from the European patent publication No.0.086.025. Also, the use of these particular IBV's in inactivated combined vaccines was disclosed in this latter publication. However, it was not recognized up till the present invention that these spontaneously hemagglutinating IBV's are particularly well suited for use in live combined vaccines together with other viruses infectious to poultry as well.

DETAILED DESCRIPTION

According to the invention the vaccine comprises at least one other virus infectious to poultry but different from IBV.

This latter so-called other virus can be selected from, for example, NDV-, IBDV, MDV, other avian Herpes Viruses, FPV, avian Adeno Viruses and avian Reo Viruses.

Particularly well suited IBV strains for use according to the present invention are strain Ma5 (working seed of which is deposited on Dec. 15, 1987 under no. VR 2199 with American Type Culture Collection (ATCC), 12301 Parklawn Drive, Rockville, Md. 20852, U.S.A., and strains D274, D1466, D580, 246G and 249G (deposited at the Collection Nationale de Cultures de Microorganismes at the Institut Pasteur at Paris under no.'s. I-216, I-217, I-218, I-215 and I-214, respectively). Strains Ma5 and 246G belong to the Massachusetts serotypes, strain D580 belongs to the Connecticut type, whereas the remaining mentioned IBV strains belong to other different serotypes, respectively.

The viruses for use in the preparation of the vaccines according to the present invention can be grown in any medium suitable for culture of avian viruses. Particularly suitable is the growing of these viruses in embryonated SPF chicken eggs or on a cell culture, preferably from avian tissues.

Thus grown viruses can be brought together in the desired ratios and the resulting mixture can be divided into quantities suitable for vaccination of either a single bird or a multitude of birds.

The live vaccine may be prepared in the form of a suspension or may be lyophilized.

In lyophilized vaccines it is preferable to add one or more stabilizers. Suitable stabilizers are for example SPGA (described by Bovarnick (1950) J.Bacteriology 59; 509), carbohydrates (such as sorbitol, mannitol, starch, sucrose, dextran, glucose), proteins (such as albumin or casein) or degradation products thereof, protein containing agents (such as bovine serum or skimmed milk) and buffers (such as alkali metal phosphates). Optionally, one or more compounds having adjuvant activity may be added too. Suitable adjuvants are for example aluminum hydroxide, phosphate or oxide, mineral oils (such as Bayol F®, Marcol 52® and saponins.

Optionally the viruses can be attenuated. This attenuation can be performed by adaptation of the viruses to embryonated eggs or a cell culture (preferably chicken embryo kidney cells) and passaging the virus in those cultures e.g. 10 to 200 times.

The live vaccines according to the invention may be administered for example by muscular, subcutaneous or in ovo injection, eye drop, nose drop, drinking water or spray methods, and preferably at an age varying from one day old to the point of lay (about 18 weeks).

For administration to one-day-old chickens advantageously use may be made of vaccines containing the mentioned Ma5 strain or a strain derived therefrom which also shows spontaneous hemagglutination of chicken erythrocytes .

For live vaccines a dosage of each of the respective virus strains may be used in a range of 3logEID$_{50}$ to 7logEID$_{50}$ per bird, preferably between about 4logEID$_{50}$ to 5logEID$_{50}$ per bird.

EXPERIMENTAL

EXAMPLE I

Comparison of two live NDV/IBV combination vaccines and separate vaccines of the two respective viruses Experimental design: one-day-old SPF chickens were divided into 8 groups and placed in negative pressure isolators.

Group I was vaccinated by eye-drop with $10^4$ EID$_{50}$/bird of the Ma5 strain (HA$^+$ strain).

Group II was vaccinated by eye-drop with $10^4$ EID$_{50}$/bird of the IBV-Mildvac-M (a commercial available vaccine for one-day-old broiler chickens produced by Intervet America Inc.; HA$^-$ strain).

Group III was vaccinated by eye-drop with minimal $10^{5.8}$ EID$_{50}$/bird of the NDV-B1 strain (a commercial available vaccine of a Hitchner type NDV strain—Intervet America Inc.).

Groups IV and V were vaccinated by eye-drop with a combination of the IBV-Mildvac-M and the NDV-B1 strain (with the same dose as in the single vaccination).

Groups VI and VII were vaccinated by eye-drop with a combination of the Ma5 strain and the NDV-B1 strain (with the same dose as in the single vaccination).

Group VIII was vaccinated by eye-drop with negative allantoic-fluid and served as controls.

Challenge was performed at 21 post-vaccination with either the USDA-IBV-M41-challenge strain (group I, II, IV, VI and part of VIII) or the USDA-NDV-challenge strain (group III, V, VII and part of VIII).

From the birds which received a challenge with the USDA-IBV-M41-challenge strain, clinical symptoms were recorded four days post-challenge; the birds were then killed and tracheas were collected for virus recovery attempts and for observation of cilial movement. The birds which received a challenge with the USDA-NDV-challenge strain were observed for mortality and clinical signs during 10 days post-challenge.

Results

In table 1 percentile protection against USDA-IBV-M41-challenge strain as measured by virus recovery, ciliostasis and clinical signs four days post-challenge are given.

TABLE 1

| Vaccine | Ciliostasis four days p.c. | Virus recovery four days p.c. | Clinical signs four days p.v. |
|---|---|---|---|
| Ma5 | 95* | 60* | 100* |
| Mildvac-M | 85 | 60 | 100 |
| Ma5/NDV-B1 | 85 | 70 | 100 |
| Mildvac-M/ NDV-B1 | 70 | 15 | 80 |
| Negative allantoic fluid | 0 | 0 | 70 |

*percentage of birds protected against challenge three weeks post- vaccination as measured by different criteria.

The Ma5 (HA$^+$) strain, in combination with a NDV-strain gives a better protection against a challenge with a M41-challenge strain then the Mildvac-M (HA$^-$) strain. No significant difference in protection could be observed between the groups which received a NDV challenge. The protection in all cases was sufficient: more than 90% of the chicks were protected in all groups.

EXAMPLE II

One day old commercial broiler chickens were divided in five groups and placed in isolators.

2 groups were vaccinated with the combination H120/Clone 30 (one group by coarse spray, the other group by eye-drop) and 2 other groups were vaccinated with the combination Ma5/Clone 30 (one group by coarse spray; one group by eye-drop); one group remained as unvaccinated controls.

Clone 30 is a NDV vaccine, commercially available from Intervet .

Four and eight days post-vaccination 6 birds per group were removed, clinical symptoms were recorded and their tracheas were examined in the ciliostasis test.

Five weeks post-vaccination the birds vaccinated by eye-drop were submitted to a challenge with the M41-challenge strain ($10^6$ EID$_{50}$ per bird, eye-drop). Four days after the M41-challenge, clinical symptoms were recorded and tracheas were taken for the ciliostasis test.

The birds vaccinated by course spray were submitted to a NDV-challenge five weeks post-vaccination (NDV-Herts-challenge strain, $10^7$ EID$_{50}$ per bird; intramuscular) and clinical symptoms and mortality were recorded daily during 12 days.

Results: Tables 2, 3, 4 and 5 show the results of the above experiments. It is clear, that the combination with the spontaneously hemagglutinating IB strain (Ma5) provides better protection against challenge with both a M41-challenge strain and a NDV-challenge strain than the combination with the IB strain which is not spontaneously hemagglutinating chicken erythrocytes (H120).

TABLE 2

CLINICAL SYMPTOMS POST VACCINATION
VACCINATION AT ONE DAY OLD
CLINICAL SYMPTOMS (SNEEZING, GURGLING)
AT FOUR AND
EIGHT DAYS POST-VACCINATION (P.V.)
TITER AT DAY OF VACCINATION EXPRESSED
AT HI $^2$LOG; M41
7.6; NDV 5.2.

| | PERCENTAGE OF BIRDS WITH CLINICAL SYMPTOMS | |
|---|---|---|
| VACCINE | FOUR DAYS P.V. | EIGHT DAYS P.V. |
| H120 (HA$^-$)/CLONE 30 EYE-DROP | 0 | 33 |
| H120 (HA$^-$)/CLONE 30 SPRAY | 0 | 17 |
| MA5 (HA$^+$)/CLONE 30 EYE-DROP | 0 | 17 |
| MA5 (HA$^+$)/CLONE 30 SPRAY | 0 | 0 |
| NONE | 0 | 0 |

TABLE 3

| CILIA STOPPING TEST POST VACCINATION VACCINATION AT ONE DAY OLD CILIA STOPPING TEST AT FOUR AND EIGHT DAYS POST-VACCINATION (P.V.) TITER AT DAY OF VACCINATION AS HI $^2$LOG: M41 7.6; NDV 5.2 | | |
|---|---|---|
| | PERCENTAGE OF BIRDS WITH CILIA STOPPING | |
| VACCINE | FOUR DAYS P.V. | EIGHT DAYS P.V. |
| H120 (HA$^-$)/CLONE 30 EYE-DROP | 17 | 33 |
| H120 (HA$^-$)/CLONE 30 SPRAY | 0 | 17 |
| MA5 (HA$^+$)/CLONE 30 EYE-DROP | 0 | 0 |
| MA5 (HA$^+$)/CLONE 30 SPRAY | 0 | 17 |
| NONE | 0 | 0 |

TABLE 4

| PROTECTION COMBINED VACCINE AGAINST ND VACCINATION AT ONE DAY OLD CHALLENGE WITH A NDV-CHALLENGE STRAIN FIVE WEEKS P.V. | |
|---|---|
| VACCINE | CHALLENGE WITH NDV-CHALLENGE STRAIN PERCENTAGE OF ANIMALS PROTECTED |
| H120 (HA$^-$)/CLONE 30 SPRAY | 83 |
| MA5 (HA$^+$)/CLONE 30 SPRAY | 100 |
| NONE | 0 |

TABLE 5

| PROTECTION COMBINED VACCINE AGAINST IB VACCINATION AT ONE DAY OLD CHALLENGE WITH A M41 CHALLENGE STRAIN FIVE WEEKS P.V. | | |
|---|---|---|
| | FOUR DAYS POST CHALLENGE WITH A M41-CHALLENGE STRAIN | |
| VACCINE | PERCENTAGE OF ANIMALS WITH CLINICAL SYMPTOMS POST-CHALLENGE | PERCENTAGE OF ANIMALS PROTECTED AS MEASURED IN THE CILIOSTASIS TEST |
| H120 (HA$^-$)/CLONE 30 EYE-DROP | 30 | 58 |
| MA5 (HA$^+$)/CLONE 30 EYE-DROP | 0 | 100 |
| NONE | 83 | 0 |

EXAMPLE III

Two hundred and fifty one-day-old SPF chickens (SPAFAS ®) were divided into four groups each containing fifty chickens and placed into negative pressure isolators. The birds were then vaccinated with the following strains:

group I: Ma5; $10^4$ $EID_{50}$/animal (eye-drop) HA$^+$ strain group II: Mildvac-M (Mass-type; B48 strain, commercially available from Intervet America Inc.); $10^4$ $EID_{50}$/animal (eye-drop); HA$^-$ strain group III: IB-vac-M (Mass-type; Connaught strain, commercially available from Intervet America Inc.); $10^4$ $EID_{50}$/animal (eye-drop); HA$^-$ strain group IV: Negative allantoic fluid; 0.1 ml/animal (eye-drop).

Five weeks post vaccination all groups were submitted to a challenge with the M41-challenge strain. Five days post challenge clinical symptoms from ten birds per group were recorded, the birds were then killed and tracheas were removed for virus reisolation and observation of ciliary activity. Seven days post-challenge the remaining birds in all groups were necropsied.

Results

TABLE 6

| Recovery of challenge virus 5 days p.c. | | |
|---|---|---|
| Vaccine | Virus recovery | % protected |
| Ma5 | 0/10* | 100 |
| Mildvac | 2/10 | 80 |
| IB-vac-M | 0/10 | 100 |
| Negative AAF | 10/10 | 0 |

*ratios express number of birds yielding virus per total number of birds.

TABLE 7

| Clinical symptoms 5 days p.c. | |
|---|---|
| Vaccine | % of birds with clinical symptoms p.c. |
| Ma5 | 0 |
| Mildvac-M | 20 |
| IB-vac-M | 10 |
| Negative AAF | 90 |

TABLE 8

| Ciliostasis test 5 days p.c. | | |
|---|---|---|
| Vaccine | +/total | % protected |
| Ma5 | 5/5* | 100 |
| Mildvac-M | 4/5 | 80 |
| IB-vac-M | 5/5 | 100 |
| Negative AAF | 0/5 | 0 |

*ratios express number of animals with a mean ciliary activity greater than 2 per total number of birds.

TABLE 9

| Necropsy results 7 days p.c. | |
|---|---|
| Vaccine | % of birds with air sacculitis |
| Ma5 | 0 |

TABLE 9-continued

| | Necropsy results 7 days p.c. |
|---|---|
| Vaccine | % of birds with air sacculitis |
| Mildvac-M | 0 |
| IB-vac-M | 16.6 |
| Negative AAF | 42.8 |

Conclusion: the Ma5 strain, which displays spontaneous hemagglutination gives a better protection against challenge than the two $HA^-$ strains compared belonging to the same serotype. Furthermore, in experiments not shown in the present example it was found that the Ma5 strain has outstanding properties also in combination vaccines together with other IBV strains.

We claim:

1. A live combined vaccine for immunizing poultry against viral infectious diseases comprising an effective amount of Infectious Bronchitis Virus VR 2199 or a spontaneously hemagglutinating strain derived therefrom, and at least one other virus infectious to poultry but different from IBV.

2. Vaccine according to claim 1 wherein said other virus is selected from the group consisting of Newcastle Disease Virus, Infectious Bursal Disease Virus, Egg Drop Syndrome Virus, Marek's Disease Virus, Avian Encephalomyelitis Virus, Reticuloendoteleosis Virus, avian Herpes Viruses, Leucosis Virus, avian Adeno Viruses and avian Reo Viruses.

3. An essentially pure culture of Infectious Bronchitis Virus belonging to the strain deposited with ATCC, at Rockville, Md., U.S.A. under accession no. VR 2199 or a spontaneously hemagglutinating strain derived therefrom.

4. A method of immunizing poultry against avian viral diseases, comprising administering an effective amount of a live combined virus according to claim 1.

5. A process for the preparation of a live combined vaccine according to claim 1 comprising bringing together said VR 2199 or a spontaneously hemagglutinating strain derived therefrom and at least one other virus infectious to poultry but different from IBV.

6. A live virus vaccine for immunizing poultry against viral infectious bronchitis comprising an immunogenically effective amount of viable Infectious Bronchitis Virus of ATCC strain VR 2199 or a spontaneously hemagglutinating strain derived therefrom.

7. A method of immunizing poultry against avian viral infectious bronchitis comprising administering an effective amount of the vaccine according to claim 6.

8. Vaccine according to claim 2, wherein said other virus is a Newcastle Disease Virus.

9. Vaccine according to claim 2, wherein said other virus is an avian Herpes Virus.

10. Vaccine according to claim 9, wherein the avian Herpes Virus is an Infectious Laryngotracheitis Virus.

* * * * *